United States Patent [19]

Beltrop

[11] Patent Number: 5,008,922
[45] Date of Patent: Apr. 16, 1991

[54] SAMPLE CASSETTE

[75] Inventor: Herbert Beltrop, Hamm, Fed. Rep. of Germany

[73] Assignee: Krupp Polysius AG, Fed. Rep. of Germany

[21] Appl. No.: 427,295

[22] Filed: Oct. 26, 1989

[30] Foreign Application Priority Data

Nov. 3, 1988 [DE] Fed. Rep. of Germany ... 8813765[U]

[51] Int. Cl.$^5$ .................. H05G 1/00; H05G 1/02; G03B 42/02
[52] U.S. Cl. .................. 378/208; 378/204; 378/195; 378/180
[58] Field of Search .................. 279/1 SG, 23 R, 24, 279/29, 80, 79; 294/33; 269/454, 455, 545, 465; 378/210, 208, 177, 204, 20, 195, 180

[56] References Cited

FOREIGN PATENT DOCUMENTS 128362 5/1985 Sweden .................. 279/23

Primary Examiner—Edward P. Westin
Assistant Examiner—Don Wong
Attorney, Agent, or Firm—Learman & McCulloch

[57] ABSTRACT

The invention relates to a cassette for supporting a material sample, the cassette including a housing and a retaining assembly for retaining the sample in the housing. The retaining assembly includes a plurality of retaining members adapted to be disposed about the periphery of the sample for movement radially thereof, a biasing spring encircling the retaining members for biasing the retaining members into engagement with the sample, and a cover supported by the housing for securing the retaining members and the biasing member within the housing.

11 Claims, 1 Drawing Sheet

SAMPLE CASSETTE

The invention relates to a sample cassette, and in particular to a cassette adapted to receive a sample of melt for subsequent analysis on an X-ray spectrometer.

BACKGROUND OF THE INVENTION

A known cassette consists of an annular housing into which the sample is placed from one board side. The sample is secured in the cassette by means of a retaining spring which is locked in the cassette by a rotary movement through 90°.

A disavantage of the csassettes of the prior art is that they are not readily adapted for use in conjunction with automated processes and, more specifically, for use by robots. Indeed, for the fully automatic insertion of a sample of melt into an X-ray spectrometer it is an important prerequisite that the setting up of the sample in the sample cassette be preformed by robots.

SUMMARY OF THE INVENTION

The object of the invention, therefore, is to construct a sample cassette in such a way that the sample can be placed in the cassette in a simple manner, and in particular by means of robot, and can be reliably fixed in the cassette. Accordingly, the subject invention is directed toward a cassette having a housing for receiving and supporting a meterial sample and retaining means for retaining the sample in the housing. The cassette is characterized in that the retaining means includes a plurality of ring segments adapted for disposition about the periphery of the sample and movable perpendicular to the direction of insertion of the sample into the housing for engaging the sample about the periphery thereof. The retaining means also includes biasing means for biasing the retaining members into engagment with the sample, and a cover operatively supported by the housing for securing the retaining means and the biasing means within the housing. Finally, the cover portion includes an opening through which the sample may be introduced to the housing.

THE DRAWINGS

The invention will be described in greater detail below with the aid of the accompanying drawings wherein:

FIG. 1 is a half cross sectional view through a sample cassette with the sample placed in it, FIG. 2 is a half cross sectional top view taken along the line II—II in FIG. 1.

DETAILED DESCRIPTION

Figure 1:
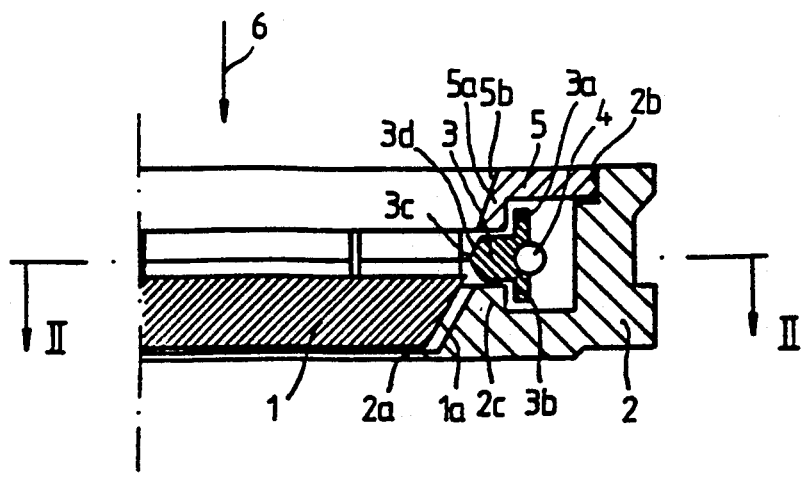
Figure 2:
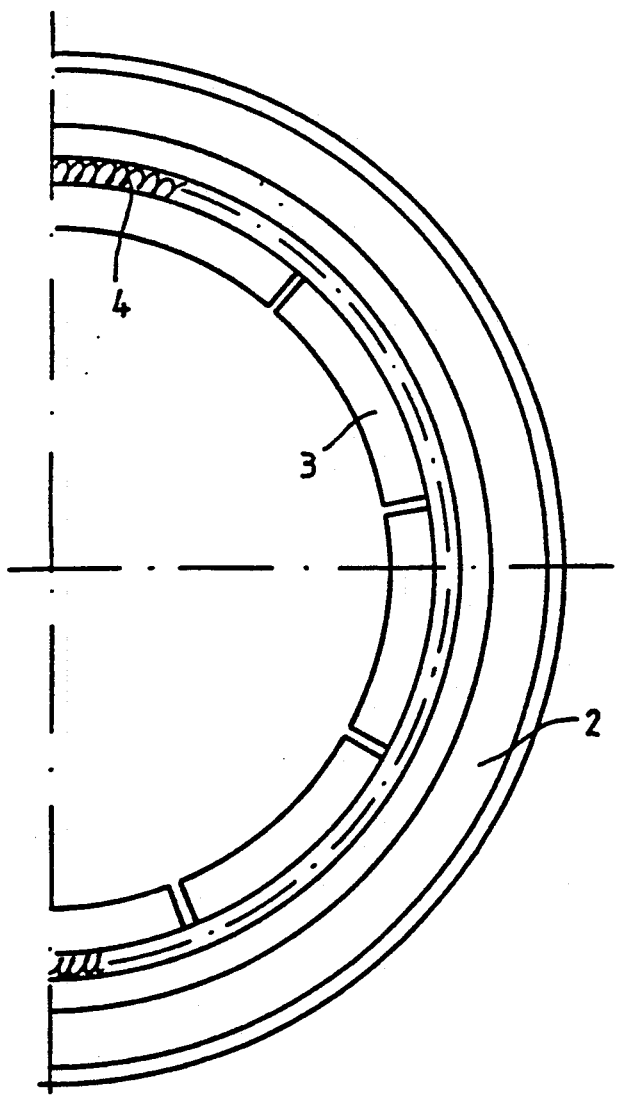

The sample cassette which is illustrated in the drawings is employed for insertion of a sample of melt 1 into an X-ray spectrometer. It consists essentially of a housing 2 and a retaining means. The retaining means includes a plurality of retaining members or ring segments 3, a biasing helical spring 4, and a cover portion 5.

The housing 2 is of annular contruction and is open broad sides. In the region of one broad side (the lower one in FIG. 1) the housing 2 form a cavity side of which is a flange 2a forming a circular opening, the diameter of which is somewhat smaller than the diameter of the sample 1. In the region of the other broad side the housing 2 is provided with an opening 2b, the diameter of which is substantially greater than the diameter of the sample 1 and which serves to receive the cover 5.

The ring segments 3, nine of which for example are evenly distributed over the entire periphery, are movable in the housing 2 in the radial direction and thus at right angles to the direction of insertion of the sample 1 as shown by the arrow 6 in FIG. 1. They are pushed radially inwards by the helical spring 4 which rests on the outer periphery and encircles all of the ring segments 3.

The cover is also of annular construction and has a flange 5a which points in the direction of the ring segments 3. The housing 2 is provided with a flange 2c which lies opposite the flange 5a.

The ring segements 3 have on their outer face a widened portion in the form of two annular projections 3a, 3b with which they come to rest on the flanges 5a and 2c respectively of the cover 5 or the housing 2 when there is no sample in the housing.

For the introduction of the sample 1 into the housing 2, the housing 2 is brought into the the turned position shown in FIG. 1 so that the sample 1, which is for example picked up by a robot by means of a suction device, can be inserted into the housing 2 of the sample cassette from above in the direction of the arrow 6. In the way, the ring segments 3 yield to such an extent that the sample 1 can pass the inner edge 3c of the ring segments 3. The sample 1 then rests on the part of the housing 2 which defines the openings 2a, and the ring segments 3 engage behind the sample 2 and reliably secure it in its position in the housing.

The housing 2 with the inserted sample 1 can then be turned by the robot, placed on a conveyor belt and delivered to the X-ray spectrometer.

As can be seen from FIG. 1, the outer periphery 1a of the sample 1 is constructed in the shape of a truncated cone. The cover 5 and the ring segments 3 have inner casing surfaces 5b and 3d respectively which are also constructed in the shape of a truncated cone. In this way, it is possible to introduce the sample 1 into the housing 2 with a light pressure so that the ring segments 3 yield elastically until they lock the sample so that it is held firmly and with its true measurements in the housing 2 of the sample cassette.

I claim:

1. A cassette for a material sample, said cassette comprising a housing for supporting the sample; and retaining means fore retaining the sample in the cassette housing, said retaining means including a plurality of segments adapted to enclose the sample when the said sample is in said housing, said segments being movable relative to said housing toward clamping engagement with said sample, biasing means encircling said segments for biasing them in a direction toward engagment with the sample, and a cover supported by said cassette housing.

2. A cassette as set forth in claim 1 wherein said cassette housing and said cover are annular and said segments are arcuate.

3. A cassette as set forth in claim 2 wherein each of said arcuate segments has an outer periphery, said biasing means comprising a circular spring engaging said outer periphery of each of said arcuate segments.

4. A cassette as set forth in claim 3 wherein each of said arcuate segments has an inner periphery presenting a casing surface in the shape of a truncated cone.

5. A sample cassette comprising a housing having a cavity therein for accommodation of a sample; a cover for at least partially closing said cavity; a plurality of retaining elements within said housing encircling said cavity; and a circular biasing spring encircling said retaining elements and yieldably biasing said retaining elements in a direction to engage and clamp a sample in said cavity.

6. A cassette according to claim 5 wherein said cavity is circular and wherein each of said retaining elements comprises an arcuate segment.

7. A cassette according to claim 5 wherein each of said retaining elements has a beveled surface underlying said cover and extending in a direction to overlie a peripheral edge of a sample in said cavity.

8. A cassette according to claim 5 wherein said cover has a flange extending inwardly of said cavity and each of said retaining elements has a flange engageable with the flange of said cover.

9. A cassette according to claim 5 wherein said cavity extends completely through said housing, said housing having a lip at that side of said housing opposite said cover for engaging a sample in said cavity, said cover comprising an annular member having at its inner periphery a flange extending inwardly of said cavity to overlie a peripheral portion of said sample.

10. A cassette according to claim 9 wherein each of said retaining elements has a peaked surface extending into said cavity, said peaked surface having its apex at level to overlie a sample in said cavity.

11. A cassette according to claim 10 wherein each of said retaining elements has a flange at that edge remote from said cavity, said flange on said retaining elements being engageable with said housing and said cover to limit movement of said retaining elements in a direction inwardly of said cavity.

* * * * *

UNITED STATES PATENT AND TRADEMARK OFFICE
CERTIFICATE OF CORRECTION

PATENT NO. : 5,008,922
DATED : April 16, 1991
INVENTOR(S) : Herbert Beltrop

It is certified that error appears in the above-identified patent and that said Letters Patent is hereby corrected as shown below:

Column 1, line 10, change "board" to --broad--; line 14, change "csassettes" to --cassettes--; line 20, change "preformed" to --performed--; line 29, change "meterial" to --material--; line 62, after "forms a cavity" insert --at one--.

Column 2, line 19, cancel "the" (second occurrence); line 46, change "fore" to --for--; line 48, cancel "the" (second occurrence); line 66, after "for" insert --the--.

Column 4, line 9, after "at" insert --a--.

Signed and Sealed this

Fifteenth Day of September, 1992

Attest:

DOUGLAS B. COMER

Attesting Officer

Acting Commissioner of Patents and Trademarks